US00PP31775P2

(12) United States Plant Patent
van Vloten

(10) Patent No.: US PP31,775 P2
(45) Date of Patent: May 19, 2020

(54) ***THUJA* PLANT NAMED 'THUCAVLO'**

(50) Latin Name: *Thuja occidentalis*
Varietal Denomination: Thucavlo

(71) Applicant: Casey van Vloten, Aldergrove (CA)

(72) Inventor: Casey van Vloten, Aldergrove (CA)

( * ) Notice: Subject to any disclaimer, the term of this patent is extended or adjusted under 35 U.S.C. 154(b) by 0 days.

(21) Appl. No.: 16/501,301

(22) Filed: Mar. 21, 2019

(51) Int. Cl.
*A01H 7/00* (2006.01)

(52) U.S. Cl.
USPC ..... Plt./213

(58) Field of Classification Search
USPC ..... Plt./213
CPC ..... A01H 7/00
See application file for complete search history.

*Primary Examiner* — Keith O. Robinson
(74) *Attorney, Agent, or Firm* — Penny J. Aguirre

(57) ABSTRACT

A new cultivar of *Thuja occidentalis* plant named 'Thucavlo' that is characterized by its dense foliage, its dwarf growth habit, and its upright and globular growth habit with a broadly acute apex.

2 Drawing Sheets

Botanical classification: *Thuja occidentalis.*
Varietal denomination: 'Thucavlo'.

CROSS REFERENCE TO A RELATED APPLICATION

This application is related to a European plant breeders' rights application filed on Jan. 1, 2018, application No. 2018/0001. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Thuja occidentalis* and will be referred to hereafter by its cultivar name, 'Thucavlo'. 'Thucavlo' represents a new western cedar, an evergreen tree grown for landscape use.

The inventor discovered 'Thucavlo' as a naturally occurring branch mutation of 'Smaragd' (not patented) in December 2012 that was growing in a production field in Aldergrove, British Columbia, Canada.

Asexual propagation of the new cultivar was first accomplished by the Inventor using stem cuttings in November 2013 in Aldergrove, British Columbia, Canada. Asexual propagation by stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Thucavlo' as a unique cultivar of *Thuja.*

1. 'Thucavlo' exhibits dense foliage.
2. 'Thucavlo' exhibits a dwarf growth habit.
3. 'Thucavlo' exhibits an upright and semi-globular growth habit with a broadly acute apex.

The parent plant of 'Thucavlo', 'Smaragd', differs from 'Thucavlo' in having a less dwarf growth habit, less dense foliage (more open), and less globular shape with a more pointed apex. 'Thucavlo' can be most closely compared to the *Thuja plicata* cultivars 'Danica' (not patented) and 'Bail John' (U.S. Plant Pat. No. 15,850). 'Danica' is similar to 'Thucavlo' in foliage color but differs from 'Thucavlo' in having a less upright and more globular plant habit. 'Bail John' is similar to 'Thucavlo' in having dense foliage and a dwarf growth habit, but differs from 'Thucavlo' in having a more pyramidal plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1). Website listings with information from direct or indirect disclosure by the Inventor include but are not limited to listings by plantipp, concept plants, and a listing entitled neuheitenschaufenster 2020 (and other related published references to the new plant showcase at IPM conference).

BRIEF DESCRIPTION OF THE DRAWINGS

The accompanying colored photographs illustrate the overall appearance and distinct characteristics of the new *Thuja*. The photographs were taken of a three-year-old plant as grown outdoors in a 21-cm container in Ederveen, The Netherlands.

Figure 1:
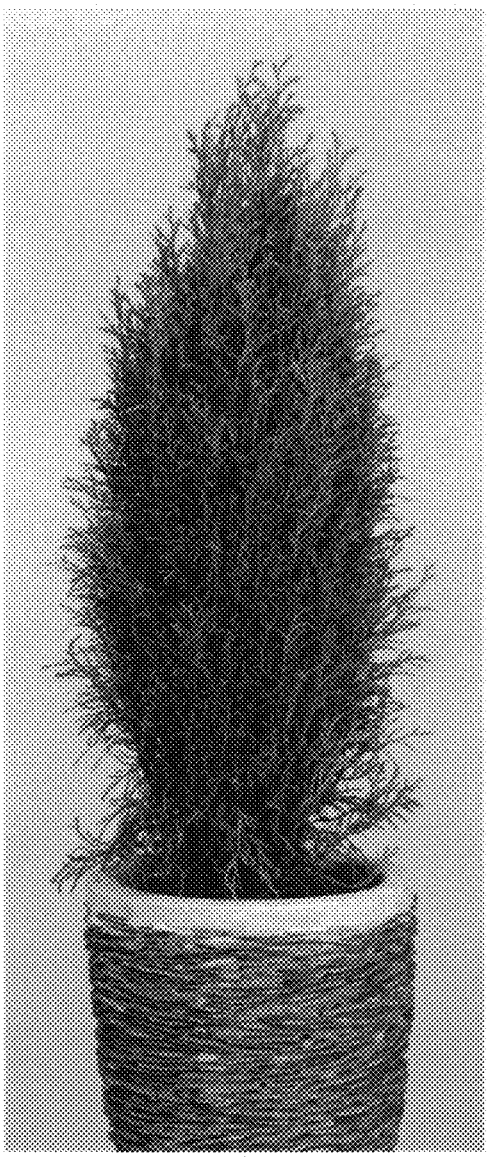
FIG. 1 provides an overall view of the plant habit of 'Thucavlo'.
Figure 2:
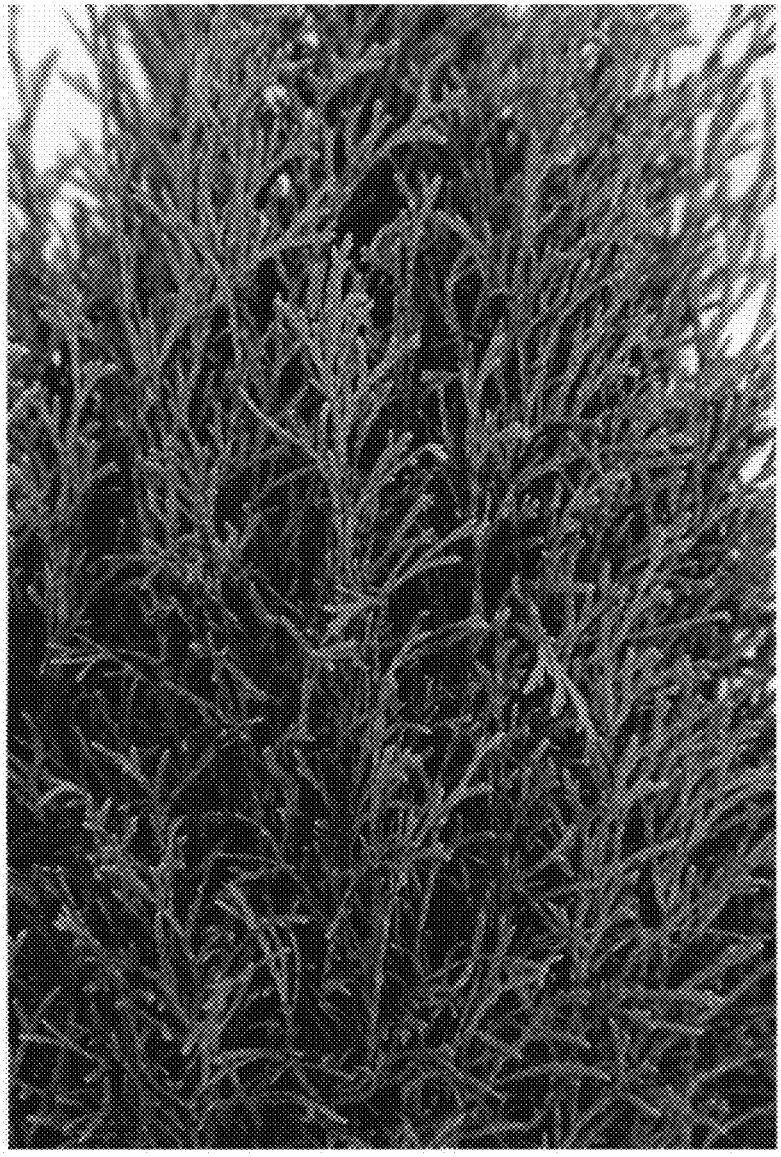
FIG. 2 provides a close-up view of the foliage of 'Thucavlo'.

The colors in the photographs are as close as possible with the photographic and printing technology utilized and the color values cited in the detailed botanical description accurately describe the colors of the new *Thuja*.

DETAILED BOTANICAL DESCRIPTION

The following is a detailed description of the new cultivar as taken from three-year-old plant as grown outdoors in a 20-cm circular container in Ederveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Coniferous, evergreen tree.

*Plant habit*.—Upright and semi-globular with a broadly acute apex.

*Plant size*.—An average of 64.8 cm in height and 27.1 cm in width as grown in a 20-cm container and reaches 1.5 to 1.75 m in height and 40 to 50 cm in spread as a mature plant in the landscape.

*Hardiness*.—At least in U.S.D.A. Zones 3 to 11.

*Diseases and pests*.—No susceptibility or resistance to diseases or pests has been observed.

*Root description*.—Fibrous, moderately thick.

*Propagation*.—Stem cuttings.

*Growth rate*.—Moderately vigorous.

*Root development*.—A rooted cutting is produced in 8 to 10 weeks, a young plant is produced in about 5 months from a rooted cutting.

Branch description:

*Branch quantity*.—Average of 7 main branches and 75 lateral branches.

*Branch shape*.—Rounded.

*Branch aspect*.—Average of 85° from vertical.

*Branch size*.—Lateral branch average of 30.7 cm in length and 4 mm in diameter.

*Branch surface*.—Densely covered with scale-like leaves that are very slightly glossy.

*Branching*.—Densely, freely branching.

*Branch arrangement*.—Alternate.

*Branch strength*.—Strong.

*Internode length*.—Average of 1.4 cm.

*Branch color*.—Young branches; between 144A and N144A, mature stems; 164A and N199D, older bark; 176A and 200B to 200C.

Foliage description:

*Leaf arrangement*.—Opposite.

*Leaf attachment*.—Sessile.

*Leaf shape*.—Oblong, folded.

*Leaf division*.—Simple.

*Leaf base*.—Decurrent.

*Leaf aspect*.—Average of 30° to lateral branch.

*Leaf apex*.—Apiculate.

*Leaf venation*.—Not distinguishable, coloration matches leaf coloration.

*Leaf margins*.—Entire.

*Leaf fragrance*.—Slight evergreen fragrance when crushed.

*Leaf surface*.—Upper and lower surfaces; matte, non-rugose.

*Leaf color*.—Mature upper surface N144A, lower surface 143B.

*Leaf size*.—Average of 3.5 mm in length, 1.5 mm in width.

*Leaf quantity*.—Average of 8,000 scale-like leaves per lateral branch.

Cone description: Neither male nor female cones have been observed to date.

It is claimed:

1. A new and distinct cultivar of *Thuja* plant named 'Thucavlo' as herein illustrated and described.

* * * * *